United States Patent [19]

Mark et al.

[11] Patent Number: 4,535,191

[45] Date of Patent: Aug. 13, 1985

[54] DIHYDRIC PHENOLS

[75] Inventors: Victor Mark, Evansville; Charles V. Hedges, Mt. Vernon, both of Ind.

[73] Assignee: General Electric Company, Mt. Vernon, Ind.

[21] Appl. No.: 582,946

[22] Filed: Feb. 23, 1984

[51] Int. Cl.³ .................. C07C 39/16; C07C 39/24
[52] U.S. Cl. .................... 568/727; 568/722; 568/723; 568/726; 568/728
[58] Field of Search ............ 568/722, 723, 726, 727, 568/728

[56] References Cited

U.S. PATENT DOCUMENTS

| | | | |
|---|---|---|---|
| 2,602,822 | 7/1952 | Schwarzer et al. | 568/723 |
| 3,057,928 | 10/1962 | Frederick et al. | 568/723 |
| 4,365,098 | 12/1982 | Mark et al. | 568/726 |

FOREIGN PATENT DOCUMENTS

| | | | |
|---|---|---|---|
| 02380 | 7/1982 | PCT Int'l Appl. | 568/723 |
| 02381 | 7/1982 | PCT Int'l Appl. | 568/723 |

Primary Examiner—Werren B. Lone
Attorney, Agent, or Firm—Myron B. Kapustij; Martin B. Barancik

[57] ABSTRACT

Novel polycarbonates are provided which exhibit rubbery and elastomeric properties which are the polymerized reaction products of:
(i) a carbonate precursor; and
(ii) at least one dihydric phenol represented by the general formula

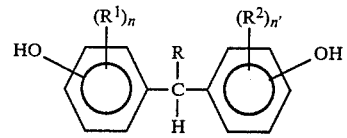

wherein
R is selected from straight chain alkyl radicals containing from 8 to about 30 carbon atoms;
each $R^1$ is independently selected from halogen monovalent hydrocarbon, and monovalent hydrocarbonoxy radicals;
each $R^2$ is independently selected from halogen, monovalent hydrocarbon, and monovalent hydrocarbonoxy radicals; and
n and n' are independently selected from whole numbers having a value of from 0 to 4 inclusive.

13 Claims, No Drawings

DIHYDRIC PHENOLS

This is a division of copending application Ser. No. 447,030, filed 12/6/82, U.S. Pat. No. 4,446,285.

BACKGROUND OF THE INVENTION

Polycarbonates are well known termoplastic materials which, due to their many advantageous properties, find use as thermoplastic engineering materials in many commercial and industrial applications. The polycarbonates exhibit, for example, excellent properties of toughness, flexibility, impact strength, optical clarity, and the like. The polycarbonates can generally be prepared by reacting a dihydric phenol with a carbonate precursor to provide generally linear polymers consisting of the residues of the dihydric phenols linked to one another through carbonate linkages. These polycarbonates and their preparation are disclosed, inter alia, in U.S. Pat. Nos. 3,028,365; 3,275,601; 3,334,154 and 3,915,926.

It would, however, be very advantageous in certain applications if polycarbonates could be provided which in addition to exhibiting all of the properties commonly possessed by presently available polycarbonate resins, also exhibited the characteristics or properties of rubbery material, i.e., elasticity, shape memory, and the like. It is the object of the instant invention to provide polycarbonates which exhibit rubbery characteristcs while simultaneously retaining, at least to a significant degree, substantially all or most of the other advantageous properties of presently available polycarbonates.

SUMMARY OF THE INVENTION

In accordance with the instant invention there are provided novel polycarbonates exhibiting, at least to a significant degree, substantially all or most of the other advantageous properties of polycarbonate resins and simultaneously exhibiting rubbery properties such as, for example, elasticity and shape memory. These novel carbonate polymers are obtained by the coreaction of, as essential reactants, (i) a carbonate precursor, and (ii) at least one certain specific dihydric phenol.

The dihydric phenols which are utilized as essential coreactants in the preparation of the novel polycarbonates of the instant invention may be represented by the general formula

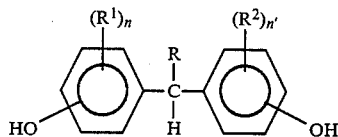

wherein R represents a long straight chain alkyl radical containing from 8 to about 30 carbon atoms; $R^1$ is independently selected from halogen, monovalent hydrocarbon, and monovalent hydrocarbonoxy radicals; $R^2$ is independently selected from halogen, monovalent hydrocarbon, and monovalent hydrocarbonoxy radicals; and n and n' are independently selected from whole numbers having a value of from 0 to 4 inclusive.

DESCRIPTION OF THE INVENTION

In one embodiment of the instant invention there are provided novel high molecular weight aromatic carbonate polymers exhibiting a great degree of rubbery properties, e.g., elasticity, shape memory, low second order glass transition temperatures (Tg), and the like, obtained by reacting (i) a carbonate precursor with (ii) at least one novel dihydric phenol represented by the general formula

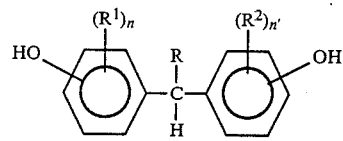

wherein:

R is selected from long straight chain alkyl radicals containing from 8 to about 30 carbon atoms;

$R^1$ is independently selected from halogen, monovalent hydrocarbon, and monovalent hydrocarbonoxy radicals;

$R^2$ is independently selected from halogen, monovalent hydrocarbon, and monovalent hydrocarbonoxy radicals; and n and n' are independently selected from whole numbers having a value of from 0 to 4 inclusive.

In the novel dihydric phenol compounds of Formula I when more than one $R^1$ substituent is present, i.e., when n is 2–4, they may be the same or different. The same is true for the $R^2$ substituent. Likewise, if both $R^1$ and $R^2$ substituents are present they may be the same or different. The positions of the hydroxyl groups and $R^1$ and $R^2$ on the aromatic nuclear residues can be varied in the ortho, meta, or para positions and the groupings can be in a vicinal, asymmetrical or symmetrical relationship, where two or more ring carbon atoms of the aromatic hydrocarbon residue are substituted with $R^1$ and/or $R^2$ and hydroxyl groups.

The monovalent hydrocarbon radicals represented by $R^1$ and $R^2$ include the alkyl, aryl, alkaryl and aralkyl radicals. The monovalent hydrocarbonoxy radicals represented by $R^1$ and $R^2$ include the alkoxy and aryloxy radicals.

The preferred halogen radicals represented by $R^1$ and $R^2$ are chlorine and bromine. The preferred alkyl radicals represented by $R^1$ and $R^2$ are the straight chain and branched alkyl radicals containing from 1 to about 6 carbon atoms. Preferred aryl radicals represented by $R^1$ and $R^2$ are those containing 6 to 12 carbon atoms, e.g., phenyl and naphthyl. Preferred alkaryl and aralkyl radicals represented by $R^1$ and $R^2$ are those containing from 7 to about 14 carbon atoms, e.g., benzyl, ethylphenyl, and the like. Preferred alkoxy radicals represented by $R^1$ and $R^2$ are those containing from 1 to about 6 carbon atoms, while the preferred aryloxy radicals are those containing from 6 to 12 carbon atoms.

The novel dihydric phenols of Formula I are prepared by the coreaction of a particular aldehyde compound and a phenol in the presence of a catalyst, preferably an acid catalyst. The particular aldehyde reactant is selected from aldehydes represented by the general formula

wherein R is as defined above. The phenol reactants are selected from phenols represented by the general formulae

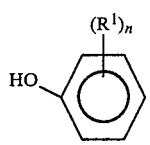   III.

and

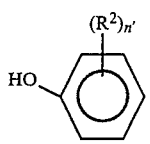   IV.

wherein $R^1$, $R^2$, n and n' are as defined above.

In order to obtain the novel dihydric phenols of Formula I one mole of an aldehyde of Formula II is reacted with one mole of a phenol of Formula III and one mole of a phenol of Formula IV in the presence of an acid catalyst, e.g., hydrochloric acid, hydrobromic acid, sulfuric acid, methanesulfonic acid, trifluoromethane sulfonic acid, benzene sulfonic acid, toluene sulfonic acid, polyphosphoric acid, and ion exchange resin acids such as polystyrene sulfonic acid, and the like, under conditions of temperature and pressure such that the coreaction between the aldehyde and the phenol will readily occur to form the novel dihydric phenols. Generally, the reaction proceeds very satisfactorily at one atmosphere of pressure and at room temperature. The amount of the acid catalyst utilized is a catalytic amount. By catalytic amount is meant an amount effective to catalyze the reaction between the aldehyde and the phenol to produce the dihydric phenol. Generally, this amount is in the range of from about 0.1 to about 10 weight percent of acid.

The phenols of Formulae III and IV may be the same. In such a case one mole of the aldehyde of Formula II is reacted with two moles of the phenol.

It is often advantageous to use an excess of the phenol reactant and to recover or remove the unreacted phenol at the end of the reaction.

As stated above, the alkyl radical represented by R in Formula I is a straight chain alkyl radical containing from 8 to about 30 carbon atoms. It is critical to the present invention that said alkyl radical contain from 8 to about 30 carbon atoms. If said alkyl contains from 8 to about 30 carbon atoms the resultant polycarbonate exhibits rubbery properties, has a smooth and soft surface, especially in thin films, and also, in certain cases exhibits a leathery appearance and texture. If said alkyl radical contains less than 8 carbon atoms the resultant polycarbonate does not exhibit, to any appreciable degree, these rubbery or leathery characteristics. If, on the other hand, said alkyl radical contains more than about 30 carbon atoms some of the other advantageous properties of the resultant polycarbonate begin to be adversely affected. Thus, for example, if said alkyl radical contains more than about 30 carbon atoms the resultant polycarbonate begins to exhibit opaqueness, brittleness, and the heat distortion temperature under load is very significantly adversely affected.

Some nonlimiting illustrative examples of the dihydric phenols represented by Formula I include:

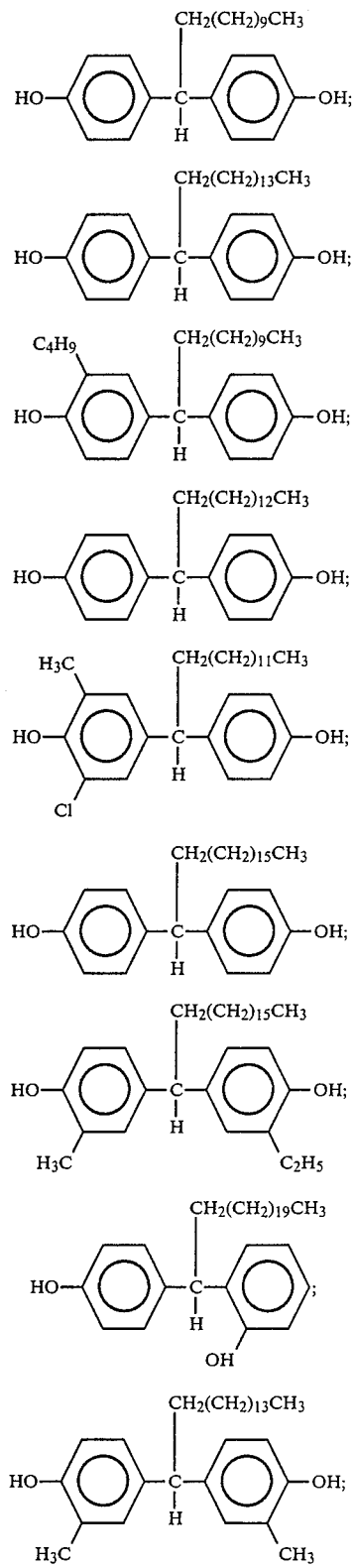

and the like.

In the preparation of the carbonate polymers of the instant invention only one dihydric phenol of Formula I may be used in the case where a carbonate homopolymer is desired. It is, of course, possible to utilize two or more different dihydric phenols of Formula I where a carbonate copolymer is desired. Thus, when the term dihydric phenol is used herein, it is meant to include mixtures of two or more dihydric phenols as well as individual dihydric phenols.

The carbonate precursor can be a carbonyl halide, a diaryl carbonate, or a bishaloformate. The preferred carbonate precursors are the carbonyl halides. The carbonyl halides include carbonyl chloride, carbonyl bromide, and mixtures thereof. The preferred carbonyl halide is carbonyl chloride, also known as phosgene.

The novel carbonate polymers of the instant invention contain repeating structural units represented by the general formula

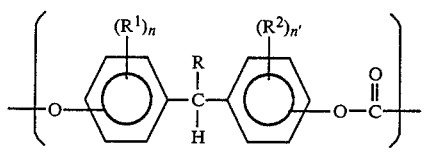

V.

wherein R, $R^1$, $R^2$, n and n' are as defined above.

As previously mentioned, R is an alkyl radical containing from 8 to about 30 carbon atoms.

These high molecular weight aromatic carbonate polymers generally have a weight average molecular weight in the range of from about 10,000 to about 200,000, preferably from about 20,000 to about 100,000, and more preferably from about 25,000 to about 50,000.

One method of preparing the high molecular weight aromatic carbonate polymers of the instant invention, when employing phosgene as the carbonate precursor, involves passing phosgene into a reaction mixture containing water and a non-miscible organic solvent, at least one dihydric phenol of Formula I, an acid acceptor, a catalyst, and a molecular weight regulator.

A suitable acid acceptor may be either organic or inorganic in nature. A suitable organic acid acceptor is a tertiary amine and includes such materials as pyridine, triethylamine, dimethylaniline, tributylamine, etc. The inorganic acid acceptor may be one which can be a hydroxide, a carbonate, or a bicarbonate of an alkali or alkaline earth metal. An inorganic acid acceptor is preferred when an aqueous solvent system is used.

The catalysts which can be employed may be any of the well known catalysts that aid the polymerization reaction of the dihydric phenol with the phosgene. Suitable catalysts include tertiary amines, quaternary phosphonium compounds, quaternary ammonium compounds, amidines, and the like.

The molecular weight regulators employed may be any of the well known compounds which regulate the molecular weight of the polycarbonate by the chain-stopping or terminating mechanism. These compounds include, but are not limited to, phenol, t-butyl phenol, and the like.

The temperature at which phosgenation proceeds may vary from below 0° C. to above 100° C. The phosgenation reaction proceeds satisfactorily at temperatures from room temperature (25° C.) to about 50° C. Since the reaction is exothermic, the rate of phosgene addition may be used to control the reaction temperature.

The carbonate polymers of the instant invention are highly flexible, exhibit elastomeric or rubbery properties, and have a smooth and relatively soft surface. Some of these polymers, particularly those wherein R contains from about 11 to about 15 carbon atoms, also exhibit a leathery hand. Generally, the greater the number of carbon atoms present in R, the greater the rubbery or elastomeric properties exhibited by the polycarbonates. These polycarbonates, particularly those wherein R contain more than 15 carbon atoms, also exhibit shape memory, i.e., when they are bent, twisted, or deformed they will return to their original shape or form. The instant polymers also exhibit, at the same time, substantially most of the advantageous characteristics of presently available polycarbonates.

The instant polycarbonates, due to their rather unique properties, are particularly useful in the film form as coatings or interlayers in laminar structures.

The carbonate polymers of the instant invention may optionally have admixed therewith certain commonly known and used additives such as antioxidants; antistatic agents; glass fibers; fillers; ultraviolet radiation absorbers such as the benzophenones and the benzotriazoles; hydrolytic stabilizers such as the epoxides disclosed in U.S. Pat. Nos. 3,489,716; 4,138,379 and 3,839,247, all of which are incorporated herein by reference; color stabilizers such as the organophosphites disclosed in U.S. Pat. Nos. 3,305,520 and 4,118,370, both of which are incorporated herein by reference; and flame retardants.

Some particularly useful flame retardants are the alkali and alkaline earth metal salts of sulfonic acids. These types of flame retardants are disclosed in U.S. Pat. Nos. 3,933,734; 3,948,851; 3,926,908; 3,919,167; 3,909,490; 3,953,396; 3,931,100; 3,978,024; 3,953,399; 3,917,559; 3,951,910 and 3,940,366, all of which are incorporated herein by reference.

Another embodiment of the instant invention is a carbonate copolymer obtained by reacting (i) a carbonate precursor, (ii) at least one dihydric phenol represented by Formula I, and (iii) at least one dihydric phenol represented by the general formula

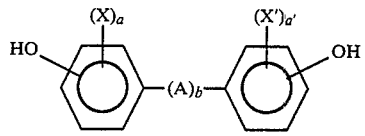

VI.

wherein A represents an alkylene radical, preferably one containing from 1 to about 6 carbon atoms; a cycloalkylene radical, preferably one containing from 4 to about 12 carbon atoms; an alkylidene radical, preferably one containing from 1 to about 6 carbon atoms; a cycloalkylidene radical, preferably one containing from 4 to about 12 carbon atoms; —S—; —S—S—; —O—;

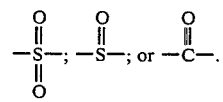

In Formula VI each X is independently selected from halogen radicals, monovalent hydrocarbon radicals, alkoxy radicals, and aryloxy radicals. Each X' in Formula VI is independently selected from halogen radicals, monovalent hydrocarbon radicals, alkoxy radicals, and aryloxy radicals. The letters a and a' in Formula VI are independently selected from whole numbers having a value of from 0 to 4 inclusive, and b is 0 or 1.

The monovalent hydrocarbon radicals represented by X and X' include alkyl radicals, preferably those containing from 1 to about 6 carbon atoms; aryl radicals, preferably those containing from 6 to 12 carbon atoms; alkaryl radicals, preferably those containing from 7 to about 14 carbon atoms; and aralkyl radicals, preferably those containing from 7 to about 14 carbon atoms. The preferred alkoxy radicals represented by X and X' are those containing from 1 to about 6 carbon atoms. The preffered aryloxy radicals are those containing from 6 to 12 carbon atoms.

In the dihydric phenol compounds represented by Formula VI when more than one X substituent is present, they may be the same or different. The same is true for the X' substituent. Likewise, the X and X' substituents may be the same or different. Where b is zero in Formula VI the aromatic rings are directly joined with no intervening alkylene or other hydrocarbon bridge. The positions of the hydroxyl groups and X and X' on the aromatic nuclear residues can be varied in the ortho, meta, or para positions and the groupings can be in a vicinal, asymmetrical or symmetrical relationship, where two or more ring carbon atoms of the aromatic hydrocarbon residue are substituted with X or X' and hydroxyl groups.

Some nonlimiting illustrative examples of suitable dihydric phenols of Formula VI include:
2,2-bis(4-hydroxyphenyl)propane (bisphenol-A);
1,1-bis(4-hydroxyphenyl)cyclohexane;
2,2-bis(4-hydroxyphenyl)hexane;
bis(3-methy-4-hydroxyphenyl)methane;
1,1-bis(3-methyl-4-hydroxyphenyl)ethane;
3,3-bis(3,5-dibromo-4-hydroxyphenyl)hexane;
bis(3,5-diisopropyl-4-hydroxyphenyl)sulfoxide;
bis(3,5-dimethyl-4-hydroxyphenyl)sulfone;
3,3'-diethyl-4,4'-dihydroxydiphenyl; and the like.
A variety of additional dihydric phenols of Formula VI are disclosed in U.S. Pat. Nos. 2,999,835; 3,028,365; 3,153,008; 2,288,282; 2,739,171 and 3,148,172, all of which are incorporated herein by reference.

The amount of the dihydric phenol of Formula I utilized in this embodiment is an amount effective to impart elastomeric or rubbery properties to said copolymer. Generally this amount ranges from about 0.5 to about 90 weight %, preferably from about 1 to about 80 weight %, and more preferably from about 5 to about 70 weight %, based on the total amount of the dihydric phenols of Formulae I and VI utilized. Generally, if less than about 0.5 weight % of the dihydric phenol of Formula I is used there is no noticeable increase in the elastomeric or rubbery properties of the copolymer. If more than about 1 weight percent of the dihydric phenol of Formula I is utilized, the resulting copolymer begins to exhibit elastomeric or rubbery properties to a significant degree.

The copolymers of the instant invention also exhibit improved impact strengths as compared to presently available polycarbonates, e.g., polycarbonates derived from Bisphenol-A. It is known in the art to provide polycarbonate compositions exhibiting improved impact strengths by admixing with the polycarbonate resin certain impact modifiers. While the addition of these impact modifying compounds to the polycarbonate resin results in polycarbonate compositions exhibiting improved impact strengths, it also sometimes adversely affects some of the other advantageous properties of the polycarbonates such as, for example, optical clarity, thermal aging, color, and thermal stability, and often results in phase separation. With the copolymers of the instant invention, since no additive need be added to improve the impact strength, these aforementioned disadvantages are avoided.

The copolycarbonates of the instant invention also exhibit improved surface appearance. That is to say, the surface of these copolymers is relatively smooth and soft to the touch as compared to presently available polycarbonates, e.g., those derived from Bisphenol-A.

The upper limit of the amount of the dihydric phenol of Formula I that may be used depends upon the properties that it is desired for the copolymer to exhibit. Thus, for example, if it is desired to produce a copolymer exhibiting a great degree of rubbery or elastomeric properties and a very smooth and soft surface a relatively large amount of the dihydric phenol of Formula I is utilized. If a copolymer exhibiting a lesser degree of rubbery or elastomeric properties is desired, a smaller amount of the dihydric phenol of Formula I is used. Generally, if a relatively large amount of the dihydric phenol of Formula I is utilized, especially one where the alkyl group represented by R contains a large number of carbon atoms, while the elastomeric character of the copolymer is enhanced the heat distortion temperature under load (DTUL) of the copolymer is decreased.

In order to obtain a copolymer exhibiting an optimum combination of properties, e.g., improved impact strength, elastomeric properties, and good heat distortion temperatures, the amount of the dihydric phenol of Formula I used, relative to the total amount of phenols of Formulae I and VI used, is an amount which is effective to improve the impact strength of the copolymer and to impart rubbery or elastomeric properties thereto but insufficient to significantly lower the heat distortion temperature of the copolymer. This amount is generally in the range of from about 1 to about 25 weight percent.

The carbonate polymers of this embodiment of the instant invention, i.e., those obtained by reacting (i) a carbonate precursor, (ii) a dihydric phenol of Formula I, and (iii) a dihydric phenol of Formula VI contain the following repeating structural units:
structural unit of Formula V; and

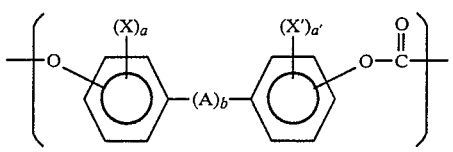

VII.

wherein A, X, X',b,a and a' are as defined above.

The amount of the repeating structures V and VII will depend upon the amount of the dihydric phenols of Formula I and VI used. Thus, for example, if a relatively large amount of the dihydric phenol of Formula VI is used relative to the amount of the dihydric Phenol of Formula I used, the copolymer will contain a relatively large amounts of repeating units of Formula VII vis-a-vis the repeating structural units of Formula V.

The procedure for preparing the carbonate copolymers of the instant invention is generally similar to that described hereinafore for the preparation of the carbonate polymers.

The carbonate copolymers of the instant invention may optionally contain admixed therewith the various additives described hereinafore such as antioxidants, fillers, antistatic agents, glass fibers, ultraviolet radiation absorbers, hydrolytic stabilizers, flame retardant agents, and the like.

Yet another embodiment of the instant invention is a physical blend of (i) at least on carbonate polymer obtained by the reaction of (a) a carbonate precursor, and (b) at least one dihydric phenol of Formula I, and (ii) at least one carbonate polymer obtained by the reaction of (a) a carbonate precursor, and (b) at least one dihydric phenol of Formula VI.

The resulting blends, by virtue of the presence therein of the carbonate polymer derived from (i) a carbonate precursor and (ii) a dihydric phenol of Formula I, exhibit improved impact resistance, and rubbery and elastomeric characteristics as compared with carbonate polymers derived from (i) a carbonate precursor and (iii) a dihydric phenol of Formula VI such as, for example, Bisphenol-A.

These blends are prepared by first preparing the respective carbonate polymers, i.e., those derived from a carbonate precursor and the dihydric phenol of Formula I and those derived from a carbonate precursor and a dihydric phenol of Formula VI, and thereafter physically admixing the two different polymers together.

The amount of the carbonate polymer derived from a carbonate precursor and the dihydric phenol of Formula I present in these blends is an amount which is effective to improve the impact strength of the blends and to impart rubbery or elastomeric properties thereto. Generally, this amount is in the range of from about 1 to about 90 weight percent. Generally, the larger the amount of the carbonate polymer derived from a carbonate precursor and the dihydric phenol of Formula I that is present in the blends, the greater the degree of rubbery or elastomeric properties achieved by the blend. However, if relatively large amounts of the polymer derived from a carbonate precursor and the dihydric phenol of Formula I are present in the blend the heat distortion temperature of the blend is lowered. In order to obtain blends exhibiting an optimum range of properties, i.e., improved impact strengths, elastic or rubbery properties, and good heat distortion temperatures, the blends should contain an amount of the carbonate polymer derived from a carbonate precursor and the dihydric phenol of Formula I effective to improve the impact strengths of the blends and to impart thereto elastic or rubbery properties but insufficient to significantly lower the heat distortion temperatures of said blends. Generally, this amount is in the range of from about 1 to about 25 weight percent.

The blends of the instant invention may optionally contain admixed therewith the additives described hereinafore such as, for example, antioxidants, antistatic agents, glass fibers, fillers, ultraviolet radiation absorbers, color stabilizers, hydrolytic stabilizers, flame retardants, and the like.

Still another embodiment of the instant invention is a copolyester-carbonate polymer derived from (i) a carbonate precursor, (ii) at least one dihydric phenol of Formula I, and (iii) at least one difunctional carboxylic acid or a reactive derivative thereof.

Briefly stated, the copolyester-carbonates of this embodiment comprise recurring carbonate groups

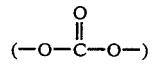

carboxylate groups

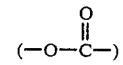

and aromatic carbocyclic groups in the linear polymer chain, in which at least some of the carboxylate groups and at least some of the carbonate groups are bonded directly to ring carbon atoms of the aromatic carbocyclic groups.

These copolyester-carbonate polymers contain ester and carbonate linkages in the polymer chain, wherein the amount of the ester linkages is in the range of from about 25 to about 90 mole percent, preferably in the range of from about 35 to about 80 mole percent.

Copolyester-carbonates in general, and methods for their preparation are disclosed in U.S. Pat. No. 3,169,121, which is hereby incorporated by reference.

In general, any difunctional carboxylic acid conventionally used in the preparation of linear polyesters may be utilized for the preparation of the copolyester-carbonates of the present invention. In general, the carboxylic acids which may be used include the aliphatic carboxylic acids, aliphatic-aromatic carboxylic acids, and aromatic carboxylic acids. These acids are disclosed in U.S. Pat. No. 3,169,121, which is hereby incorporated herein by reference.

The carboxylic acids which may be utilized in the preparation of the copolyester-carbonates generally conform to the formula $$R^3-(R^4)_q-COOH \qquad \text{VIII.}$$

wherein $R^4$ is an alkylene, alkylidene, aralkylene, araalkylidene or cycloaliphatic group; an alkylene, alkylidene or cycloaliphatic group containing ethylenic unsaturation; an aromatic group such as phenylene, biphenylene, substituted phenylene, and the like; two or more aromatic groups connected through non-aromatic linkages such as alkylene or alkylidene groups; and the like. $R^3$ is either a carboxyl or a hydroxyl group. The letter q represents one where $R^3$ is a hydroxyl group and either zero or one where $R^3$ is a carboxyl group.

Preferred difunctional carboxylic acids are the aromatic carboxylic acids, i.e., those wherein q is one, $R^3$ is a carboxyl or hydroxyl group, and $R^4$ is an aromatic group such as phenylene, biphenylene, naphthylene, substituted phenylene, and the like. The preferred aromatic carboxylic acids are those represented by the general formula

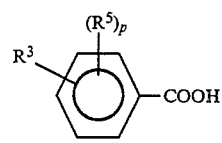

IX.

wherein $R^3$ is as defined above; p represents a whole number having a value of from 0 to 4 inclusive; and $R^5$ represents an inorganic atom such as chlorine, bromine, etc, an organic group such as a monovalent hydrocarbon group such as alkyl, aryl, aralkyl, alkaryl, or a cycloaliphatic group; or an inorganic group such as the nitro group, etc. When more than one $R^5$ substituent is present, they may be the same or different.

Mixtures of these difunctional carboxylic acids can also be employed and where the term difunctional carboxylic acid is used herein, mixtures of such materials are considered to be included.

Preferred aromatic difunctional carboxylic acids are isophathlic acid and terephtahlic acid, and mixtures thereof. A particularly useful mixture of isophthalic acid and terephathlic acid is one wherein the ratio by weight of isophathlic acid and terephthalic acid is in the range of from about 1:10 to about 10:1.

Rather than utilizing the difunctional carboxylic acids per se it is possible, and sometimes even preferred, to employ their reactive derivatives such as, for example, the acid halides. The preferred derivatives of the carboxylic acids are the acid chlorides. Thus, for example, instead of using terephthalic acid, isophthalic acid or mixtures thereof, terephthaloyl chloride, isophthaloyl chloride, or mixtures of isophthaloyl chloride and terephthaloyl chloride may be employed.

When the difunctional acid utilized is a dicarboxylic acid or a reactive derivative thereof the copolyester-carbonates of the instant invention will contain repeating units represented by the structures:

structure V; and

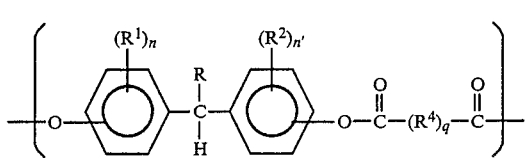

wherein R, $R^1$, $R^2$, $R^4$, n, n' and q are as defined above. When the difunctional acid or its reactive derivative used is a hydroxy carboxylic acid or its reactive derivative the copolyester-carbonates of the instant invention will contain repeating units represented by the structures:

structure V;

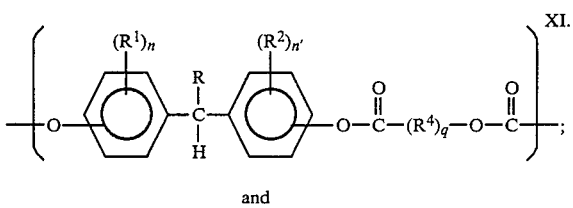

and

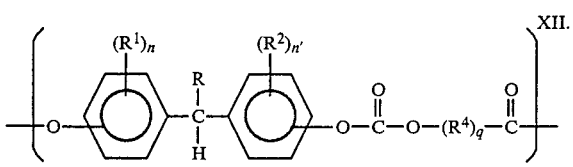

wherein R, $R^1$, $R^2$, $R^4$, q, n, and n' are as defined above. Where both hydroxy carboxylic acids and dicarboxylic acids or their reactive derivatives are utilized as the acid component the copolyester-carbonates of the instant invention will contain units of Formulae V, X, XI, and XII. The copolyester-carbonates of the instant invention thus contain at least one of the units represented by Formula V and at least one of the units represented by Formula X or XI and XII, and may contain as many as 500 or more of each of the foregoing units.

One of the methods of preparing the copolyester-carbonates of the instant invention involves the heterogeneous interfacial polymerization system utilizing an aqueous caustic solution, an organic water immiscible solvent, at least one dihydric phenol of Formula I, at least one difunctional carboxylic acid of Formula VIII or a reactive derivative thereof, a catalyst, a molecular weight regulator, and a carbonate precursor. A preferred heterogeneous interfacial polymerization system is one which utilizes phosgene as the carbonate precursor and methylene chloride or chlorobenzene as the organic solvent.

Another useful method for preparing the copolyester-carbonate polymers of the instant invention involves the use of an organic solvent system wherein the organic solvent system may also function as an acid acceptor, at least one dihydric phenol of Formula I, at least one difunctional carboxylic acid of Formula VIII or a reactive derivative thereof, a molecular weight regulator, a carbonate precursor. A preferred method is one utilizing phosgene as the carbonate precursor and pyridine or triethylamine as the acid acceptor-solvent component.

Generally, in both of these aforedescribed methods the difunctional carboxylic acid of Formula VIII, or its reactive derivative such as the diacid chloride, is introduced into the reaction mixture before or simultaneously with the introduction of the carbonate precursor such as phosgene.

The temperature at which the reaction proceeds may vary from below 0° C. to above 100° C. The reaction proceeds satisfactorily at temperatures from room temperature (25° C.) to 50° C. Since the reaction is exothermic, the rate of the difunctional carboxylic acid or its reactive derivative addition, or the rate of phosgene addition may be used to control the reaction temperature.

Some other useful procedures for the preparation of copolyester-carbonates in general are disclosed in U.S. Pat. No. 3,169,121, which is hereby incorporated herein by reference.

The copolyester-carbonate polymers of the instant invention exhibit rubbery or elastomeric properties, i.e., elasticity, shape memory, low second order glass transition temperatures, and have a smooth and relatively soft surface. Some of these copolyester-carbonates, particularly those wherein R contains from about 11 to about 15 carbon atoms, further exhibit a leathery hand. In general, the greater the number of carbon atoms present in R, the greater the degree of rubbery or elastomeric properties exhibited by these polymers. As mentioned previously, these copolyester-carbonates also exhibit shape memory. This is particularly true for those copolyester-carbonates which are derived from dihydric phenols of Formula I wherein R contains more than about 15 carbon atoms.

The instant copolyester-carbonates, due to their rather unique properties, are particularly useful in the form of thin films as coatings or interlayers in laminar structures.

The copolyester-carbonates of this invention may optionally have admixed therewith certain commonly known and used additives such as antioxidants, glass fibers, fillers, color stabilizers, ultraviolet radiation stabilizers, and flame retardants.

Another embodiment of the instant invention is a copolyester-carbonate polymer derived from (i) a carbonate precursor, (ii) at least one difunctional carboxylic acid or a reactive derivative thereof, (iii) at least one dihydric phenol of Formula I, and (iv) at least one dihydric phenol of Formula VI. In this embodiment, the amount of the dihydric phenol of Formula I utilized is an amount effective to impart elastomeric or rubbery properties to said copolyester-carbonate copolymer. In general, this amount ranges from about 0.5 to about 90 weight %, preferably from about 1 to about 80 weight %, and more preferably from about 5 to about 70 weight %, based on the total amount of dihydric phenols of Formulae I and VI used. Generally, if less than about 0.5 weight % of the dihydric phenol of Formula I is utilized there is no appreciable increase in the elastomeric properties of the copolymer. If more than about 1 weight % of the dihydric phenol of Formula I is employed the resulting copolyester-carbonate resins begin to exhibit elastomeric or rubbery properties to an appreciable degree.

The copolyester-carbonates of the instant invention also exhibit improved impact strengths as compared to presently available copolyester-carbonates, e.g., those derived solely from bisphenol-A. The copolyester-carbonates of this embodiment also exhibit improved surface appearance. That is to say, the surface of these polymers is relatively soft and smooth to the touch as compared with the surface appearance of conventional copolyester-carbonate resins.

The upper limit of the amount of the dihydric phenol of Formula I that may be employed depends upon the properties that it is desired for the copolyester-carbonate to exhibit. Thus, for example, if a copolymer exhibiting a great degree of elastomeric or rubbery properties and a very soft and smooth hand is desired then relatively large amounts of the dihydric phenol of Formula I are utilized. If a copolyester-carbonate resin exhibiting a lesser degree of rubbery or elastomeric properties is desired, a smaller amount of the dihydric phenol of Formula I is employed. Generally, if a relatively large amount of the dihydric phenol of Formula I is employed, especially one where the alkyl groups represented by R contain a large amount of carbon atoms in the linear chain, while the rubbery or elastomeric properties of the copolyester-carbonate copolymer are enhanced the heat distortion temperature of the copolymer decreases.

In order to obtain a copolyester-carbonate copolymer exhibiting an optimum combination of properties, e.g., increased impact strength, rubbery or elastomeric properties, and good heat distortion temperatures, the amount of the dihydric phenol of Formula I utilized is an amount which is effective to improve the impact strength of the copolymer and to impart rubbery or elastomeric properties thereto but insufficient to significantly lower the heat distortion temperature of the copolymer. This amount is generally in the range of from about 1 to about 25 weight percent.

The procedure for preparing the copolyester-carbonate copolymers of the instant embodiment is in general similar to that described hereinafore for the preparation of the copolyester-carbonates derived from (i) a carbonate precursor, (ii) at least one difunctional carboxylic acid or a reactive derivative thereof, and (iii) at least one dihydric phenol of Formula I, with the exception that at least one dihydric phenol of Formula VI is present in the reaction mixture.

The copolyester-carbonate copolymers of this embodiment may optionally contain admixed therewith the commonly known and used additives such as, for example, antioxidants, color stabilizers, fillers, glass fibers, hydrolytic stabilizers, ultraviolet radiation stabilizers, flame retardants, and the like.

Yet another embodiment of the instant invention is a physical blend of (i) at least one copolyester-carbonate resin derived from (a) a carbonate precursor, (b) at least one difunctional carboxylic acid or a reactive derivative thereof, and (c) at least one dihydric phenol of Formula I (hereinafter referred to as resin A); and (ii) at least one presently available copolyester-carbonate resin which is derived from (a) a carbonate precursor, (b) at least one difunctional carboxylic acid or a reactive derivative thereof, and (c) at least one dihydric phenol of Formula VI (hereinafter referred to as resin B).

These blends, by virtue of the presence therein of copolyester-carbonate resin A, exhibit improved impact strength, and rubbery or elastomeric properties as compared with presently available copolyester-carbonate resins (e.g., copolyester-carbonate resins B).

The instant blends are prepared by first preparing the copolyester-carbonate resins A and B and thereafter physically blending or mixing these resins together in the desired amounts.

The amount of copolyester-carbonate resin A which is present in these blends is an amount effective to improve the impact strength of the blends and to impart thereto rubbery or elastomeric properties. Generally, this amount is in the range of from about 1 to about 90 percent by weight. Generally, the greater the amount of resin A that is present in these blends the greater the degree of rubbery or elastomeric properties possessed by the blends. However, if relatively large amounts of resin A are present the heat distortion temperature of the blends is significantly lowered. In order to obtain blends exhibiting an optimum balance of properties, e.g., improved impact strength, elastomeric or rubbery properties, and good heat distortion temperatures, the blends should contain an amount of resin A effective to improve the impact strength of the blends and to impart thereto elastomeric or rubbery properties but insufficient to significantly lower the heat distortion temperatures of the blends. Generally, this amount is in the range of from about 1 to about 25 weight percent.

The blends of the instant invention may optionally contain admixed therewith the commonly known and used additives such as, for example, antioxidants, antistatic agents, color stabilizers, hydrolytic stabilizers, glass fibers, fillers, ultraviolet radiation stabilizers, flame retardants, and the like.

Also included within the scope of the instant invention are the high molecular weight thermoplastic randomly branched polycarbonates and copolyester-carbonates. The randomly branched polycarbonates are prepared by coreacting with the carbonate precursor and the dihydric phenol of Formula I a minor amount, preferably between 0.05 and 2.0 mol percent based on the quantity of dihydric phenol used, of a polyfunctional organic compound. The copolyester-carbonates are prepared by coreacting with the carbonate precursor, the difunctional carboxylic acid or a reactive derivative thereof, and the dihydric phenol of Formula I a minor amount of a polyfunctional organic compound. The polyfunctional organic compounds useful in making the branched polycarbonates and copolyester-carbonates are disclosed in U.S. Pat. Nos. 3,635,895; 4,001,184 and 4,204,047, all of which are incorporated herein by reference. These polyfunctional organic compounds are generally aromatic in nature and contain at least three functional groups which may be hydroxyl, carboxyl, carboxylic anhydride, haloformyl, or mixtures thereof. Some illustrative non-limiting examples of these polyfunctional compounds include trimellitic anhydride, trimellitic acid, trimellityl trichloride, 4-chloroformyl phthalic anhydride, pyromellitic dianhydride, mellitic acid, mellitic anhydride, trimesic acid, benzophenonetetracarboxylic acid, benzophenonetetracarboxylic anhydride, and the like. Also included with the scope of the instant invention are blends of linear polycarbonates and branched polycarbonates; and blends of linear copolyester-carbonates and branched copolyester-carbonates.

The copolyester-carbonates, preferably the aromatic copolyester-carbonates, of the instant invention generally have a weight average molecular weight in the range of from about 10,000 to about 200,000, preferably from about 20,000 to about 100,000, and more preferably from about 20,000 to about 50,000.

The polycarbonates of the instant invention also have a weight average molecular weight in the range of from about 10,000 to about 200,000, preferably from about 20,000 to about 100,000, and more preferably from about 20,000 to about 50,000.

PREFERRED EMBODIMENT OF THE INVENTION

In order that those skilled in the art may better understand how the present invention may be practiced, the following examples are given by way of illustration, and not by way of limitation. In the following examples, unless otherwise specified, all parts and percentages are by weight.

The following examples illustrate the preparation of the novel dihydric phenols of Formula I of the instant invention.

EXAMPLE 1

This example illustrates the preparation of octadecylidenebisphenol.

into a two liter three necked flask, equipped with an electric stirrer, reflux condenser, thermometer and addition funnel, were placed 594.6 grams (6 moles) of phenol and 214.8 grams (0.8 mole) of octadecylaldehyde (stearaldehyde, m.p. 38° C.). The reaction mixture was then heated to 42° C. and stirred untill a clear solution resulted. Concentrated aqueous hydrochloric acid was then added dropwise while keeping the reaction mixture between 45° and 50° C. The progress of the reaction was monitored by gas chromatographic analysis, which indicated that after the addition of approximately 30 ml. of the hydrochloric acid the reaction was essentially complete in about 3-5 hours, and that the product consisted of 3.5% 2,2'-, 25.4% 2,4'-, and 71.1% of 4,4'-octadecylidenebisphenol, as shown by their gas chromatographic elution times of 28.91, 29.41, and 30.28 minutes, respectively, while the p-cumylphenol control emerged at 14.74 minutes. During the addition of the hydrochloric acid solids were formed, which thickened the reaction mixture, but the mixture was still stirable. Stripping of the catalyst, water and excess phenol in aspirator vacuum yielded the above isomeric mixture as a yellow residue in nearly quantitative yields.

EXAMPLE 2

This example illustrates the preparation of 4,4'-octadecylidenebisphenol.

Into a reaction flask described in Example 1 were charged 941.0 grams (10 moles) of phenol and 50 ml. of concentrated aqueous hydrochloric acid. After melting the phenol, molten octadecylaldehyde, 537.0 grams (2.0 moles), was added dropwise from an addition funnel, kept warm by a heating lamp, to the well stirred phenol-catalyst mixture during a period of about 3-4 hours while maintaining the temperature in the flask between 45° and 55° C. During the addition of the aldehyde solids began to separate out from the reaction mixture and their amount increased as the reaction progressed. After the addition of the aldehyde was completed, the thick slurry was stirred for another hour at 50°-55° C. and then filtered by suction through a sintered glass funnel, and the resulting warm filtercake was pressed until dry. Analysis by gas chromatography of the filter cake, which weighed 620 grams, indicated that it was essentially an even mixture of phenol and 4,4'-octadecylidenebisphenol. Recrystallization of the filtercake from methylenechloride yielded the pure 4,4'-octadecylidenebisphenol which was essentially free of the 2,2'- and the 2,4'-isomers, and which had a melting point of 88.0°-90.0° C.

EXAMPLE 3

This example illustrates the preparation of 4,4'-docosylidenebisphenol.

Repeating substantially the procedure of Example 1 except that the addition funnel was replaced by a gas inlet tube and the octadecylaldehyde was replaced with 259.6 grams (0.8 mole) of docosylaldehyde (behenic aldehyde, m.p. 93°-95° C.) gaseous hydrogen chloride was introduced into the warm phenol-aldehyde solution during a period of one hour. After this one hour period gas chromatography indicated the absence of the starting aldehyde and the presence of isomeric bisphenols. The solid phase, present in the phenol solution, was filtered by suction and the resulting filtercake analyzed by gas chromatography. Analysis indicated the filter cake to consist of an eabout equal mixture of phenol and 9.8% of 2,4'- and 65.8% of 4,4'-docosylidenebisphenol. Recrystallization from methylenechloride, twice, yielded essentially pure (98.5%) 4,4'docosylidenebisphenol, which had a melting point of 93.0°-95.0° C., with a gas chromatography elution time of 33.31 minutes, relative to the elution time for the p-cumylphenol control of 14.79 minutes.

EXAMPLES 4-10

Substantially repeating the procedure of Example 1, except that various other aldehydes were substituted for the octadecylaldehyde of Example 1 and the appropriate phenol precursors were substituted for the phenol of Example 1, the dihydric phenols set forth in Table I were prepared.

The following example illustrates the preparation of a polycarbonate resin falling outside the scope of the instant invention.

EXAMPLE 11

This example illustrates the preparation of a prior art polycarbonate, i.e., one derived from bisphenol-A. This example is included for comparative purposes.

Into a mixture of 2283 grams of pure 4,4'-isopropylidenediphenol (bisphenol-A) (mp 156°-157° C.; 10.0 mole grams), 5700 grams water, 9275 grams methylene chloride, 32.0 grams phenol and 10.0 grams triethylamine were introduced, at ambient temperature, 1180 grams phosgene over a period of 97 minutes while maintaining the pH of the two phase system at about 11; i.e., pH 10-12.5, by simultaneously adding a 25% aqueous sodium hydroxide solution. At the end of the addition period, the pH of the aqueous phase was 11.7 and the bisphenol-A content of this phase was less than 1 part per million (ppm) as determined by ultraviolet analysis.

The methylene chloride phase was separated from the aqueous phase, washed with an excess of dilute (0.01N) aqueous HCl and then washed three times with deionized water. The polymer was precipitated by steam and dried at 95° C. The resultant, pure bisphenol-A polycarbonate which had an intrinsic viscosity (IV) in methylene chloride at 25° C. of 0.572 dl/g., was fed to an extruder, which extruder was operated at about 550° F., and the extrudate was comminuted into pellets.

The pellets were then injection molded at about 600° F. into test bars of about 5 in. by about ½ in. by about ⅛ in. thick and about 5 in. by about ½ in. by about 1/16 in. thick.

The following examples illustrate the preparation of the novel rubbery or elastomeric polycarbonates of the instant invention.

EXAMPLE 12

Into a mixture of 340.5 grams of 4,4'-undecylidenebisphenol, 570 grams water, 927.5 grams methylene chloride, 3.2 grams phenol and 1 gram of triethylamine were introduced, at ambient temperature, 118 grams of phosgene over a period of 97 minutes while maintaining the pH of the two phase system at about 11 by simultaneously adding a 25% aqueous sodium hydroxide solution. At the end of the addition period, the pH of the aqueous phase was 11.7.

The methylene chloride phase was separated from the aqueous phase, washed with an excess of dilute (0.01N) aqueous HCl, and then washed three times with deionized water. The polymer was precipitated by steam and dried at 95° C. The resultant 4,4'-undecylidenebisphenol polycarbonate had an intrinsic viscosity in methylene chloride at 25° C. of 0.560 dl/g. and a second order glass transition temperature (Tg) of 38.9° C.

The polymer was then dissolved in methylene chloride and cast into a thin film. This film was elastomeric and exhibited a soft and smooth hand.

EXAMPLE 13

The procedure of Example 12 was substantially repeated except that the 4,4'-undecylidenebisphenol was replaced with 4,4'-dodecylidenebisphenol.

The resultant 4,4'-dodecylidenebisphenol polycarbonate had an intrinsic viscosity in methylene chloride at 25° C. of 0.603 dl/g. and a Tg of 34.4° C.

The cast film of the 4,4'-dodecylidenebisphenol polycarbonate was highly elastomeric and exhibited a quite soft and smooth hand.

EXAMPLE 14

The procedure of Example 12 was substantially repeated except that the 4,4'-undecylidenebisphenol was replaced with 4,4'-tetradecylidenebisphenol.

The resultant 4,4'-tetradecylidenebisphenol polycarbonate had an intrinsic viscosity in methylene chloride at 25° C. of 0.544 dl/g. and a Tg of 25.4° C.

The cast film of the 4,4'-tetradecylidenebisphenol polycarbonate was highly elastomeric, exhibited a smooth and soft hand, and also exhibited a leathery hand.

EXAMPLE 15

The procedure of Example 12 was substantially repeated except that the 4,4'-undecylidenebisphenol was replaced with 4,4'-octadecylidenebisphenol.

The resultant 4,4'-octadecylidenebisphenol polycarbonate had an intrinsic viscosity in methylene chloride at 25° C. of 0.374 dl/g. and a Tg of 16.6° C.

The cast film of the 4,4'-octadecylidenebisphenol polycarbonate was highly elastomeric and had a very smooth and soft hand, and exhibited shape memory.

EXAMPLE 16

The procedure of Example 12 was substantially repeated except that the 4,4'-undecylidenebisphenol was replaced with 4,4'-docosylidenebisphenol.

The resultant 4,4'-docosylidenebisphenol polycarbonate had an intrinsic viscosity in methylene chloride at 25° C. of 0.585 dl/g. and a Tg of about 10° C.

The following example illustrates the preparation of a polycarbonate falling outside the scope of the instant invention in that the alkylidene radical bridging the two aromatic residues of the bisphenol contains a relatively short carbon chain, i.e., less than 8 carbon atoms.

EXAMPLE 17

The procedure of Example 12 was substantially repeated except that the 4,4'-undecylidenebisphenol was replaced with 4,4'-propylidenebisphenol.

The resultant 4,4'-propylidenebisphenol polycarbonate had an intrinsic viscosity in methylene chloride at 25° C. of 0.508 dl/g. and a Tg of 119.0° C.

The cast film of the 4,4'-propylidenebisphenol polycarbonate was not elastomeric, and had a relatively hard hand.

The following examples illustrate the preparation of the carbonate copolymers (those derived from a dihydric phenol of Formula I, a dihydric phenol of Formula VI, and a carbonate precursor) of the instant invention.

EXAMPLE 18

Into a mixture of 2168 grams of 4,4'-isopropylidenebisphenol, 114 grams of 4,4'-dodecylidenebisphenol, 5700 grams water, 9275 grams methylene chloride, 32 grams phenol, and 10 grams triethylamine were introduced, at ambient temperature, 1180 grams phosgene over a period of 97 minutes while maintaining the pH of the two phase system at about 11 by simultaneously adding 25% aqueous sodium hydroxide solution. At the end of the addition period the pH of the aqueous phase was 11.7.

The methylene chloride phase was separated from the aqueous phase, washed with an excess of dilute (0.01N) aqueous HCl, and then washed three times with deionized water. The polymer was precipitated by steam and dried at 95° C. The resultant carbonate copolymer, which had an intrinsic viscosity in methylene chloride at 25° C. of 0.554 dl/g. was fed to an extruder, which extruder was operated at about 550° F., and the extrudate was comminuted into pellets.

The pellets were then injection molded at about 600° F. into test bars of about 5 in. by about ½ in. by about ⅛ in. thick and about 5 in. by about ½ in. by about 1/16 in. thick.

EXAMPLE 19

The procedure of Example 18 was substantially repeated except that instead of utilizing 2168 grams of 4,4'-isopropylidenebisphenol and 114 grams of 4,4'-dodecylidenebisphenol there were used 2054 grams of 4,4'-isopropylidenebisphenol and 228 grams of 4,4'-dodecylidenebisphenol.

The resultant carbonate copolymer, which had an intrinsic viscosity in methylene chloride at 25° C. of 0.574 dl/g., was fed to an extruder operating at about 550° F., and the extrudate was comminuted into pellets.

The pellets were then injection molded at about 600° F. into test bars of about 5 in. by about ½ in. by about ⅛ in. thick, and about 5 in. by about ½ in. by about 1/16 in. thick.

Various physical properties of the test samples obtained in Example 11 (the control) and Examples 18-19 were determined according to the following procedures:

Tensile Strength (TS) of the samples was determined according to ASTM D-638;

Flexural Modulus (FM) and Flexural Strength (FS) of the samples were detremined according to ASTM D-790;

Notched Izod Impact (NI) on the ⅛ inch and the 1/16 inch thick samples was determined according to ASTM D-256;

S-Tensile Strength (S-TS) of the samples was determined according to ASTM D-1822; and the Melt Flow Rate (FR) of the polymers was determined according to ASTM D-1238-70, condition O.

The results of these tests are set forth in Table II.

The following examples, with the exception of Example 20 (which illustrates a prior art bisphenol-A type polycarbonate resin and is used for comparative purposes), illustrate the preparation of the polycarbonate blends of the instant invention. These blends are comprised of (i) at least one polycarbonate derived from (a) a carbonate precursor, and (b) at least one dihydric phenol of Formula I; and (ii) at least one polycarbonate derived from (a) a carbonate precursor, and (b) at least one dihydric phenol of Formula VI.

EXAMPLE 20

This example illustrates a polycarbonate prepared from bisphenol-A and phosgene. This polycarbonate falls outside of the scope of the instant invention and is used for comparative purposes and is the control.

A polycarbonate derived from bisphenol-A and phosgene is fed to an extruder operating at about 550° F., and the extrudate was comminuted into pellets.

The pellets were then injection molded at about 600° F. into test bars of about 5 in. by about ½ in. by about ⅛ in. thick.

EXAMPLE 21

A polycarbonate resin blend was prepared comprised of 95 weight percent of a polycarbonate resin derived from bisphenol-A and phosgene, and 5 weight percent of a polycarbonate resin derived from 4,4'-dodecylidenebisphenol and phosgene.

Test bars of this blend were prepared substantially in accordance with the procedure of Example 20.

EXAMPLE 22

A polycarbonate resin blend was prepared comprised of 90 weight percent of a polycarbonate resin derived from bisphenol-A and phosgene, and 10 weight percent of a polycarbonate resin derived from 4,4'-dodecylidenebisphenol and phosgene.

Test bars of this blend were prepared substantially in accordance with the procedure of Example 20.

EXAMPLE 23

A polycarbonate resin blend was prepared comprised of 90 weight percent of a polycarbonate resin derived from bisphenol-A and phosgene; and 10 weight percent of a carbonate copolymer derived from a 50—50 weight percent mixture of bisphenol-A and 4,4'-dodecylidenebisphenol, and phosgene.

Test bars of this blend were prepared substantially in accordance with the procedure of Example 20.

EXAMPLE 24

A polycarbonate resin blend was prepared comprised of 80 weight percent of a polycarbonate resin derived from bisphenol-A and phosgene; and 20 weight percent of a carbonate copolymer derived from a 50—50 weight percent mixture of bisphenol-A and 4,4'-dodecylidenebisphenol, and phosgene.

Test bars of this blend were prepared substantially in accordance with the procedure of Example 20.

Various physical properties of the test samples obtained in Example 20 (the control) and Examples 21-24 were determined. The physical properties determined were: Tensile Strength (TS); Tensile Elongation (TE), determined according to ASTM D- 638; Flexural Strength (FS); Flexural Modulus (FM); and Melt Flow Rate (FR). The results of these tests are set forth in Table III.

The following examples illustrate the preparation of the copolyester-carbonates of the instant invention.

EXAMPLE 25

To a reactor vessel were added 400 ml. of methylene chloride, 300 ml. of water, 35.5 grams of 4,4'-dodecylidenebisphenol, 0.24 gram of phenol, and 0.28 ml. of triethylamine. At a pH of about 11, 10.2 grams of isophthaloyldichloride were added over a 15 minute period, while maintaining the pH at about 11 by the addition of 35% aqueous caustic. After the addition of the isophthaloyl dichloride 6 grams of phosgene were introduced over a 15 minute period, while controlling the pH at about 11 by the addition of 35% aqueous caustic solution. The polymer mixture was diluted with methylene chloride and the brine phase was separated. The resulting polymer containing phase was washed with HCl and then with water, and the polymer was then recovered by steam precipitation. The resultant copolyester-carbonate was found to have an intrinsic viscosity in methylene chloride of 0.599 dl/gm. and a Tg of 53.1° C.

EXAMPLE 26

To a reactor vessel there were added 400 ml. of methylene chloride, 300 ml. of water, 35.5 grams of 4,4'-dodecylidenebisphenol, 0.24 grams of phenol, and 0.28 ml. of triethylamine. At a pH of about 11, 5.1 grams of isophthaloyldichloride were added over a 15 minute period, while maintaining the pH at about 11 by the addition of a 35% aqueous caustic solution. After the addition of the isophthaloyldichloride was terminated 8.9 grams of phosgene were introduced over a 15 minute period while maintaining the pH at about 11 by the introduction of the 34% aqueous caustic solution. The polymer mixture was diluted with methylene chloride and the brine phase was separated. The resulting polymer containing phase was washed with HCl and then with water, and the polymer was recovered by steam precipitation. The resultant copolyester-carbonate polymer had an intrinsic viscosity in methylene chloride at 25° C. of 0.639 dl/gm. and a Tg of 33.5° C.

EXAMPLE 27

To a reactor vessel were added 400 ml. of methylene chloride, 300 ml. of water, 21.9 grams of octadecylidenebisphenol, 0.12 gram of phenol, and 0.14 ml. of triethylamine. At a pH of about 11, 5.1 grams of isophthaloyldichloride were added over a 15 minute period while maintaining the pH at about 11 by the addition of a 35% aqueous caustic solution. After the addition of the isophthaloyldichloride was terminated 2.8 grams of phosgene were added over a 15 minute period while maintaining the pH at about 11 by the addition of the aqueous caustic solution. The polymer mixture was diluted with methylene chloride and the brine phase was separated. The resulting polymer containing phase was washed with HCl and then with water, and the polymer was recovered by steam precipitation. The resultant copolyester-carbonate copolymer had an intrinsic viscosity in methylene chloride at 25° C. of 0.374 dl/gm. and a Tg of less than 40° C.

EXAMPLE 28

To a reactor vessel were added 400 ml. of methylene chloride, 300 ml. of water. 21.9 grams of 4,4'-octadecylidenebisphenol, 0.12 gram of phenol, and 0.14 ml. of triethylamine. At a pH of about 11 2.5 grams of isophthaloyldichloride were added over a 15 minute period while maintaining the pH at about 11 by the addition of a 35% aqueous caustic solution. After the addition of the isophthaloyldichloride was completed 5.2 grams of phosgene were added over a 15 minute period while maintaining the pH at about 11 by the addition of the caustic solution. The polymer mixture was diluted with methylene chloride and the brine phase was separated. The resulting polymer containing phase was washed with HCl and then with water, and the polymer was recovered by steam precipitation. The resultant copolyester-carbonate polymer had an intrinsic viscosity in methylene chloride at 25° C. of 0.384 and a Tg of less than 40° C.

In the copolyester-carbonates of the instant invention the degree of rubbery or elastomeric properties exhibited by the resin may be controlled, in part, by the relative amounts of the dihydric phenol of Formula I and the difunctional carboxylic acid or its reactive derivative utilized. In general, the smaller the amount of the dihydric phenol of Formula I utilized and the larger the amount of said difunctional carboxylic acid employed, the smaller the degree of rubbery or elastomeric properties exhibited by the polymer. Conversely, if more of the dihydric phenol of Formula I is employed, which results in the copolyester-carbonate polymer chain containing more of the residues of said dihydric phenol vis-a-vis the residues of the difunctional carboxylic acid, the copolyester-carbonate will exhibit a greater degree of rubbery or elastomeric characteristics. The same holds true for copolyester-carbonates which are derived from (i) a dihydric phenol of Formula I, (ii) a dihydric phenol of Formula VI, (iii) a difunctional carboxylic acid or its reactive derivative, and (iv) a carbonate precursor.

In view of this copolyester-carbonates resins can be produced which have properties tailor made to fit a particular requirement.

TABLE I

| Example No. | Aldehyde | Phenol | Bisphenol | Melting Point °C. | % Purity | Gas Chromatography Elution Time/ref.* (minutes) |
|---|---|---|---|---|---|---|
| 4 | $CH_3(CH_2)_8CH_2-\overset{O}{\underset{\|}{C}}-H$ | phenyl-OH | $HO-C_6H_4-\underset{H}{\overset{CH_2(CH_2)_8CH_3}{C}}-C_6H_4-OH$ | 72.0–76.0 | 96.0 | 24.98/14.35 |
| 5 | $CH_3(CH_2)_9CH_2-\overset{O}{\underset{\|}{C}}-H$ | phenyl-OH | $HO-C_6H_4-\underset{H}{\overset{CH_2(CH_2)_9CH_3}{C}}-C_6H_4-OH$ | 73.0–74.5 | 98.5 | 25.71/14.36 |
| 6 | $CH_3(CH_2)_9CH_2-\overset{O}{\underset{\|}{C}}-H$ | 2-methylphenyl-OH | $HO-(3-CH_3-C_6H_3)-\underset{H}{\overset{CH_2(CH_2)_9CH_3}{C}}-(3-CH_3-C_6H_3)-OH$ | 63.0–64.5 | 98.2 | 28.20/16.40 |
| 7 | $CH_3(CH_2)_9CH_2-\overset{O}{\underset{\|}{C}}-H$ | 2,6-dimethylphenyl-OH | $HO-(3,5-(CH_3)_2-C_6H_2)-\underset{H}{\overset{CH_2(CH_2)_9CH_3}{C}}-(3,5-(CH_3)_2-C_6H_2)-OH$ | 67.5–68.5 | 99.0 | 30.20/17.26 |

TABLE I-continued

| Example No. | Aldehyde | Phenol | Bisphenol | Melting Point °C. | % Purity | Gas Chromatography Elution Time/ref.* (minutes) |
|---|---|---|---|---|---|---|
| 8 | $CH_3(CH_2)_{11}CH_2-\overset{O}{\underset{\|}{C}}-H$ | phenol-OH | HO—C₆H₄—CH(CH₂(CH₂)₁₁CH₃)—C₆H₄—OH | 76.0–78.0 | 96.5 | 27.12/14.36 |
| 9 | $CH_3(CH_2)_{11}CH_2-\overset{O}{\underset{\|}{C}}-H$ | 2-methylphenol-OH | HO—(3-CH₃-C₆H₃)—CH(CH₂(CH₂)₁₁CH₃)—(3-CH₃-C₆H₃)—OH | 69.0–71.0 | 94.8 | 29.48/16.59 |
| 10 | $CH_3(CH_2)_{11}CH_2-\overset{O}{\underset{\|}{C}}-H$ | 2,6-dimethylphenol-OH | HO—(3,5-(CH₃)₂-C₆H₂)—CH(CH₂(CH₂)₁₁CH₃)—(3,5-(CH₃)₂-C₆H₂)—OH | 70.5–72.0 | 99.9 | 30.56/16.49 |

*p-cumylphenol

TABLE II

| Example No. | TS (p.s.i.) | FS (p.s.i.) | FM (p.s.i.) | S-TS (ft. lb./in.²) | FR (gm/10 min.) | NI (ft. lb./in.) ¼ in. thick | NI (ft. lb./in.) ⅛ in. thick |
|---|---|---|---|---|---|---|---|
| 11 | 9,160 | 13,800 | 342,000 | 117.3 | 4.09 | 2.38 | 14.7/80% ductility |
| 18 | 8,980 | 13,700 | 349,000 | 293.2 | 5.70 | 2.70 | 17.9/100% ductility |
| 19 | 8,936 | 13,600 | 346,000 | 260.1 | 5.36 | 2.40 | 16.9/100% ductility |

TABLE III

| Example No. | TS (p.s.i.) | TE (%) | FS (p.s.i.) | FM (p.s.i.) | FR (gm/10 min.) |
|---|---|---|---|---|---|
| 20 | 8,900 | 50 | 14,300 | 351,000 | 4.6 |
| 21 | 8,925 | 54 | 14,600 | 362,000 | 22.2 |
| 22 | 8,980 | 52 | 14,800 | 365,000 | 28.2 |
| 23 | 9,080 | 51 | 14,300 | 342,000 | 6.6 |
| 24 | 8,990 | 50 | 13,700 | 342,000 | 6.7 |

As illustrated by the data in Table II the carbonate copolymers of the instant invention (those derived from (i) a dihydric phenol of Formula I, (ii) a dihydric phenol of Formula VI, and (iii) a carbonate precursor) exhibit improved impact strengths vis-a-vis prior art polycarbonates such as, for example, bisphenol-A type polycarbonates. The data in Table II also illustrates that this improvement in impact strength is not obtained at the expense of the other advantageous properties of the polycarbonates such as flexural strength, tensile strength, and the like, but is obtained in addition thereto. The data in Table II clearly shows that the instant copolycarbonates exhibit properties such as flexural strength and tensile strength that are generally comparable to those exhibited by prior art polycarbonates such as bisphenol-A type polycarbonates. The data in Table II further shows that the carbonate copolymers of the instant invention exhibit higher flow rates, and therefore improved processability, as compared with prior art polycarbonates.

Thus, the instant carbonate copolymers, while maintaining substantially all or most of the other advantageous properties of polycarbonates, exhibit improved impact strength and processability.

The data in Table III shows that the instant polycarbonate blends, while exhibiting substantially most of the other advantageous properties of polycarbonates, also have improved flow rates, and therefore improved processability.

The foregoing detailed description has been given for clearness of understanding only and no unnecessary limitations are to be understood therefrom. The invention is not limited to the exact details shown and described, for obvious modifications will occur to those skilled in the art.

What is claimed is:

1. Dihydric phenols represented by the general formula

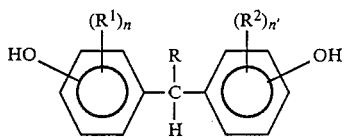

wherein:

R is selected from straight chain alkyl radicals containing from 11 to about 30 carbon atoms;

each R¹ is independently selected from halogen, monovalent hydrocarbon, and monovalent hydrocarbonoxy radicals;

each $R^2$ is independently selected from halogen, monovalent hydrocarbon, and monovalent hydrocarbonoxy radicals; and n and n' are independently selected from whole numbers having a value of from 0 to 4 inclusive.

2. The phenols of claim 1 wherein said monovalent hydrocarbon radicals are selected from alkyl, aryl, alkaryl, and aralkyl radicals.

3. The phenols of claim 2 wherein said monovalent hydrocarbon radicals are selected from alkyl radicals containing from 1 to about 6 carbon atoms.

4. The phenols of claim 1 wherein said monovalent hydrocarbonoxy radicals are selected from alkoxy and aryloxy radicals.

5. The phenols of claim 1 wherein at least one of n and n' is zero.

6. The phenols of claim 5 wherein n and n' are 0.

7. The phenols of claim 1 which are selected from 4,4'-bisphenols.

8. The phenols of claim 7 wherein n and n' are 0.

9. The phenols of claim 8 wherein said phenol is 4,4'-hexadecylidenebisphenol.

10. The phenols of claim 8 wherein said phenol is 4,4'-octadecylidenebisphenol.

11. The phenols of claim 8 wherein said phenol is 4,4'-dodecylidenebisphenol.

12. The dihydric phenols of claim 1 wherein R contains from 16 to about 30 carbon atoms.

13. The dihydric phenols of claim 12 wherein n and n' are zero.

* * * * *